United States Patent [19]

Hartenstein et al.

[11] 4,309,542
[45] Jan. 5, 1982

[54] PROCESS FOR THE O-METHYLATION OF HYDROXYAPORPHINES

[75] Inventors: Johannes Hartenstein, Stegen-Wittental; Gerhard Satzinger, Denzlingen, both of Fed. Rep. of Germany

[73] Assignee: Warner-Lambert Company, Morris Plains, N.J.

[21] Appl. No.: 971,143

[22] Filed: Dec. 19, 1978

[30] Foreign Application Priority Data

Dec. 22, 1977 [DE] Fed. Rep. of Germany ....... 2757335

[51] Int. Cl.³ ........................................... C07D 221/18
[52] U.S. Cl. .................................................. 546/075
[58] Field of Search ......................................... 546/75

[56] References Cited

U.S. PATENT DOCUMENTS 1,100,998  6/1914  Traub .................................... 546/44

FOREIGN PATENT DOCUMENTS 44-28113  11/1969  Japan ..................................... 546/75

OTHER PUBLICATIONS

Bently, The Chem. of the Morphine Alkaloids, pp. 303 & 307.
Bently "The Chem. of the Morphine Alkaloids, pp. 59, 60, Clarendon Press, Oxford, (1954).
Spath, et al., Beuichte, 62, pp. 325–331, (1929).
Bull. Soc. Chim. 39, p. 305, (1926).

*Primary Examiner*—Donald G. Daus
*Assistant Examiner*—D. B. Springer
*Attorney, Agent, or Firm*—Stephen I. Miller

[57] ABSTRACT

A process for the O-methylation of hydroxyaporphines is disclosed. This process utilizes a trimethylphenylammonium base as the alkylating agent.

8 Claims, No Drawings

PROCESS FOR THE O-METHYLATION OF HYDROXYAPORPHINES

The present invention is concerned with a new and improved process for the preparation of O-methylated derivatives of hydroxyaporphines, some of which are new.

Aporphines are alkaloids which have been known for a long time and which are derived from the following ring system:

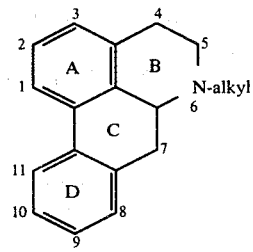

(cf. Chem. Reviews, 64, 59–79/1964).

Most of them are either obtained from plants or by partial syntheses and some of them have interesting pharmacological properties so that attempts have been made, especially in the case of the isolatable natural products, chemically to change the substituents in the aporphine skeleton. The substituents which occur most frequently in compounds of the aporphine series are hydroxyl groups and methoxy radicals so that the conversion especially of the phenolic hydroxyl groups in rings A and D into methoxy radicals is of particular interest since, in this manner, pharmacologically effective aporphine derivatives can be obtained, some of which are new, or, because of their ready availability, easily obtainable alkaloids can be converted into derivatives which were hitherto difficult to obtain. Furthermore, according to German Pat. No. 2,337,507, it is advantageous for the total synthesis of aporphines when, in the decisive step of the ring closure of benzyl-tetrahydroisoquinoline, a free hydroxyl group is present in the 7-position so that an improved methylation of phenolic hydroxyl groups supplements, in a valuable manner, the total synthesis with regard to the corresponding 1-methoxy-aporphine derivatives.

The well-known processes for the methylation of phenolic hydroxyl groups on the aporphine system, such as a basic reaction of the alkali metal phenolates in question with methylation agents, for example methyl iodide or dimethyl sulphate, do not, however, give satisfactory yields (see Arch. Pharm., 249, 643 et seq./1911) since, as is known, aporphines are very easily converted under the influence of acylating agents (see synthesis, p 249/1975), by an opening of the tetrahydropyridine ring (B), into open-chained "methines". In order to avoid this undesired side reaction, attempts have been made to carry out the alkylation with diazomethane under reaction conditions which were as neutral as possible. However, only limited success was achieved. Furthermore, a particular disadvantage of this method of alkylation is the high toxicity and especially the known cencerogenicity of diazomethane which, in addition, has a great tendency to explode, this preventing the use of diazomethane for production processes on a large scale for reasons of safety. Furthermore, in carrying out this method of alkylation, it is necessary to take into account reaction times of up to 29 days so that methylation with diazomethane also cannot be considered for large-scale use for economic reasons (cf. German Pat. No. 2,337,507, Example 13).

Since methylation agents which can be used in a neutral medium and can also be used on a large scale have hitherto not been known, the availability of correspondingly methylated aporphines in economically acceptable yields has not been possible.

Surprisingly, we have now found that trimethyl phenyl ammonium bases are outstanding O-alkylation agents for aporphines and, in spite of their strongly alkaline nature, they do not lead to a fission of the aporphine system. Without appreciable side reactions, they give the corresponding O-methylated aporphine derivatives in high yield.

It was admittedly already known that trimethyl phenyl ammonium ethylate can be used for the methylation of morphine (Bull. Soc. Chim., 39, 305/1926). However, the different behaviour of the morphine and aporphine ring systems, especially with regard to basic reaction conditions, has been pointed out many times in the literature. Since, in the case of the morphine ring system, the mere splitting of the hexahydropyrimidine ring does not result in a direct conversion into a completely aromatic phenanthrene ring system, there is here missing the strong tendency for a ring opening reaction which is typical for the aporphines. Consequently, morphine alkaloids are, in contradistinction to the aporphines, insensitive to alkaline methylation conditions.

Therefore, because of the strongly basic nature of the trimethyl phenyl ammonium bases, it was to have been expected that these would convert the aporphine ring system, with opening of the tetrahydropyridine ring, into the energy-favoured, planar and completely aromatic phenanthrene ring system. Therefore, these compounds would have been regarded as being completely useless as O-methylation agents for aporphine derivatives. This predjudiced view is also, no doubt, the reason why, until recently, the disadvantageous diazomethane (cf. German Pat. No. 2,337,507) has preferably been used.

Thus, according to the present invention, there is provided a process for the O-methylation of hydroxyaporphines, wherein the phenolic hydroxyl groups of compounds of the general formula:

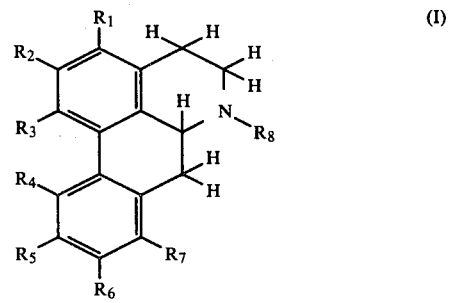

in which at least one of the symbols $R_1$ to $R_7$ represents a hydroxyl group, whereas the other symbols represent hydrogen atoms or substituents which are inert under the reaction conditions, and $R_8$ is a lower alkyl radical, are O-methylated in an inert solvent with a compound of the general formula:

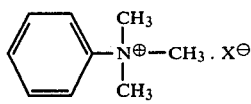

in which X⁻ is a hydroxyl group or a lower alkoxy radical, and the reaction product is then isolated and, if desired, converted into a pharmacologically acceptable salt.

According to a preferred embodiment of the process according to the present invention, the phenolic hydroxyl groups of compounds of the general formula:

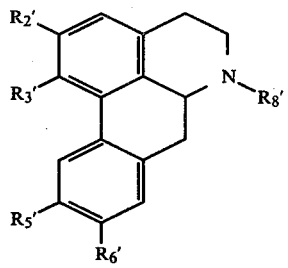

in which $R_8$ is an alkyl radical containing up to 5 and preferably up to 3 carbon atoms and at least one of the symbols $R_2'$, $R_3'$, $R_5'$ and/or $R_6'$ signifies a hydroxyl group, whereas the other symbols represent hydrogen atoms or substituents which are inert under the reaction conditions, especially methoxy radicals, or in which two of the symbols $R_2'$ and $R_3'$ or $R_5'$ and $R_6'$ can together also represent a methylenedioxy radical, are O-methylated with a compound of general formula (II) and the reaction product is isolated and, if desired, converted into a pharmacologically acceptable salt.

The O-methylation method according to the present invention is specific for acid, i.e. phenolic, hydroxyl groups, hydroxyl groups on non-aromatic rings not being methylated. The nature of other substituents possibly present hereby plays no part at all or, at most, only a subordinate part, although, of course, steric factors and especially concentrations of groups, must, under certain circumstances, be taken into account and can have a negative influence on the reaction time and yield.

The inert substituents can be, for example, alkoxy radicals containing up to 5 and preferably up to 3 carbon atoms, aryloxy radicals, for example phenoxy radicals, which can be substituted by lower alkyl or alkoxy radicals, or aralkoxy radicals, for example benzyloxy radicals. Individual positions can also be substituted by halogen atoms, such as bromine or chlorine atoms. Furthermore, two adjacent positions can also carry a methylenedioxy radical. The substituents which occur most frequently are the methoxy and methylenedioxy radicals and chlorine atoms. The nitrogen atom is usually methyl-substituted ($R_8$) but it can also carry straight-chained or branched higher homologues, for example ethyl, n-propyl, isopropyl, n-butyl or n-pentyl radicals, alkyl radicals containing up to 3 carbon atoms being preferred.

The following Table I summarises a selection of known aporphine derivatives, the phenolic hydroxyl groups of which can be methylated by means of the process according to the present invention:

1. 1-Hydroxy-2,9,10-trimethoxyaporphine (thaliporphine)
2. 1,9-Dihydroxy-2,10-dimethoxyaporphine (isoboldine)
3. 1-Hydroxy-2,10,11-trimethoxyaporphine (corydine)
4. 1,11-Dihydroxy-2,10-dimethoxyaporphine (corytuberine)
5. 1-Hydroxy-2,11-dimethoxyaporphine (isothebaine)
6. 1-Hydroxy-2-methoxy-9,10-methylenedioxyaporphine
7. 1,10-Dihydroxy-2,9-dimethoxyaporphine
8. 1-Hydroxy-2-methoxyaporphine (O-demethylnuciferine)
9. 1,10-Dihydroxy-2-methoxyaporphine (apoglaziovine)
10. 1-Hydroxy-2,10-dimethoxy-9-(3', 4'-dimethoxy)-phenoxyaporphine (cf. German Pat. No. 2,337,507; precursor of hernandaline)
11. 1,10-Dimethoxy-11-hydroxy-2,3-methylenedioxyaporphine (ocokryptine)
12. 10,11-Dihydroxyaporphine (apomorphine)
13. 2,9-Dihydroxy-1,10-dimethoxyaporphine (boldine)
14. 2-Hydroxy-1,9-10-trimethoxyaporphine (O-methylboldine)
15. 11-Hydroxy-10-methoxy-1,2-methylenedioxyaporphine (bulbocapnine)
16. 9-Hydroxy-1,2,10-trimethoxyaporphine (N-methyllaurotetanine)
17. 11-Hydroxy-1,2,10-trimethoxyaporphine (isocorydine)
18. 1,10-Dimethoxy-2,11-dihydroxyaporphine
19. 10-Hydroxy-1,2-methylenedioxyaporphine (mecambroline)
20. 9-Bromo-2,10-dimethoxy-1-hydroxyaporphine
21. 1,2-Methylenedioxy-8-hydroxyaporphine (desmethylstephanine)
22. 1,2,10-Trimethoxy-3,9-dihydroxyaporphine (The Alkaloids, 3, 135/1973).

TABLE I

| Compound No. | Position | | | | | | | |
|---|---|---|---|---|---|---|---|---|
| | $R_1$ 3 | $R_2$ 2 | $R_3$ 1 | $R_4$ 11 | $R_5$ 10 | $R_6$ 9 | $R_7$ 8 | $R_8$ 6 |
| 1 | —H | —OCH$_3$ | —OH | —H | —OCH$_3$ | —OCH$_3$ | —H | —CH$_3$ |
| 2 | —H | —OCH$_3$ | —OH | —H | —OCH$_3$ | —OH | —H | —CH$_3$ |
| 3 | —H | —OCH$_3$ | —OH | —OCH$_3$ | —OCH$_3$ | —H | —H | —CH$_3$ |
| 4 | —H | —OCH$_3$ | —OH | —OH | —OCH$_3$ | —H | —H | —CH$_3$ |
| 5 | —H | —OCH$_3$ | —OH | —OCH$_3$ | —H | —H | —H | —CH$_3$ |
| 6 | —H | —OCH$_3$ | —OH | —H | —O—CH$_2$—O— | | —H | —CH$_3$ |
| 7 | —H | —OCH$_3$ | —OH | —H | —OH | —OCH$_3$ | —H | —CH$_3$ |
| 8 | —H | —OCH$_3$ | —OH | —H | —H | —H | —H | —CH$_3$ |
| 9 | —H | —OCH$_3$ | —OH | —H | —OH | —H | —H | —CH$_3$ |
| 10 | —H | —OCH$_3$ | —OH | —H | —OCH$_3$ | * | —H | —CH$_3$ |
| 11 | —O—CH$_2$—O— | | —OCH$_3$ | —OH | —OCH$_3$ | —H | —H | —CH$_3$ |
| 12 | —H | —H | —H | —OH | —OH | —H | —H | —CH$_3$ |
| 13 | —H | —OH | —OCH$_3$ | —H | —OCH$_3$ | —OH | —H | —CH$_3$ |

TABLE I-continued

| Compound No. | R$_1$ 3 | R$_2$ 2 | R$_3$ 1 | R$_4$ 11 | R$_5$ 10 | R$_6$ 9 | R$_7$ 8 | R$_8$ 6 |
|---|---|---|---|---|---|---|---|---|
| 14 | —H | —OH | —OCH$_3$ | —H | —OCH$_3$ | —OCH$_3$ | —H | —CH$_3$ |
| 15 | —H | —O—CH$_2$—O— | | —OH | —OCH$_3$ | —H | —H | —CH$_3$ |
| 16 | —H | —OCH$_3$ | —OCH$_3$ | —H | —OCH$_3$ | —OH | —H | —CH$_3$ |
| 17 | —H | —OCH$_3$ | —OCH$_3$ | —OH | —OCH$_3$ | —H | —H | —CH$_3$ |
| 18 | —H | —OH | —OCH$_3$ | —OH | —OCH$_3$ | —H | —H | —CH$_3$ |
| 19 | —H | —O—CH$_2$—O— | | —H | —OH | —H | —H | —CH$_3$ |
| 20 | —H | —OCH$_3$ | —OH | —H | —OCH$_3$ | —Br | —H | —CH$_3$ |
| 21 | —H | —O—CH$_2$—O— | | —H | —H | —H | —OH | —CH$_3$ |
| 22 | —OH | —OCH$_3$ | —OCH$_3$ | —H | —OCH$_3$ | —OH | —H | —CH$_3$ |

*3',4'-dimethoxy-phenoxy.

The compounds Nos. 1, 2, 7, 13, 14 and 16 given in the above Table I all give the same end product, namely, 1,2,9,10-tetramethoxyaporphine, whereas compounds Nos. 3, 4, 17 and 18 give the isomeric 1,2,10,11-tetramethoxyaporphine.

The above-mentioned hydroxyaporphines are either naturally occurring and/or can be synthesised by processes which are known from the literature (cf., for example, M. Shamma, Isoquinoline Alkaloids, pub. Academic Press, 1972, pp. 194 et seq.). They can be racemates which, subsequently to the O-methylation, can be resolved in the usual manner, for example, by means of D- or L-tartaric acid or D- or L-dibenzoyltartaric acid, or they can be the enantiomers in question.

The methylation products are compounds with valuable pharmacological properties or they possess, as for example 1,2,10-trimethoxy-9-(3', 4'-dimethoxy)-phenoxy-aporphine, which is a precursor for hernandaline, a key compound for the total synthesis of the tumour-inhibiting thalicarpine (cf. German Pat. Nos. 2,337,507 and 2,161,187), importance as intermediates for the preparation of physiologically-active compounds.

The basic phenyl trimethyl ammonium compounds (II) can be used for the methylation reaction according to the present invention either as the hydroxide or as an alcoholate containing up to 5 carbon atoms in the alcoholate grouping, the methylate being preferred. Solutions of the compounds (II) can be prepared in the usual manner from the corresponding salts, such as phenyl trimethyl ammonium chloride, bromide or benzenesulphonate, by reaction with an alkali metal hydroxide or alcoholate in alcoholic solution, followed by separation of the alkali metal salt in question.

The O-methylation of hydroxyaporphines of general formula (I) can be carried out with the use of equimolar or excess amounts of the methylating agent (II) in an inert solvent at a temperature of from 100° to 150° C. and preferably of from 110° to 135° C. It is advantageous to use the methylating agent (II) in a mole ratio of 1.25 to 2 for each phenolic hydroxyl group to be methylated. The solvent used is preferably an aromatic hydrocarbon, for example, toluene, xylene or monochloro- or dichlorobenzene, alone or in mixture with one another.

According to an especially advantageous embodiment of the process according to the present invention, the reaction medium used is a mixture of a hydrocarbon, for example, toluene or xylene, and a polar solvent, for example, ethanol but especially dimethyl formamide, dimethyl sulphoxide or hexamethylphosphoric triamide. The mixing ratio can thereby be varied within wide limits. Mixtures of toluene and/or xylene with 10 to 20% by volume dimethyl formamide, dimethyl sulphoxide or hexamethyl phosphoric triamide have thereby proved to be especially advantageous, an important advantage of these solvent mixtures being the considerably shortened reaction time.

The methylation is preferably carried out by first adding an alcoholic solution of the phenyl trimethyl ammonium salt (II) to a solution or suspension of the hydroxyaporphine (I) in a solvent at the boiling temperature of the solvent/alcohol azeotrope in question and allowing the solvent/alcohol azeotrope to distil off continuously. When the addition of the phenyl trimethyl ammonium salt solution is finished, the reaction mixture is heated to the above-mentioned temperature and then maintained under reflux, the course of the reaction being monitored by thin layer chromatography. As a rule, the methylation is finished 30 to 90 minutes after commencement of the reflux boiling. In the case of polyhydroxyaporphines which are difficult to methylate, it can be advantageous, 15 to 30 minutes after commencement of the reflux boiling, again to add methylating agent under the above-described conditions and then to continue correspondingly.

For working up the reaction mixture, precipitated excess phenyl trimethyl ammonium hydroxide is filtered off and the solvent is evaporated from the filtrate. The dimethylaniline formed as by-product can be removed by steam or vacuum distillation.

The residue is taken up in an appropriate organic solvent, for example, diethyl ether, methylene chloride, chloroform or preferably benzene or toluene, and, for the removal of traces of phenolic material, is washed with a dilute aqueous alkali solution. The phenol fraction obtainable from the alkaline wash solutions after neutralisation thereof, can be used again for the methylation reaction.

After drying, the purified organic phase is evaporated in a vacuum. The methylation product is isolated from the residue either directly or possibly after previous chromatography, by crystallisation or after conversion into an appropriate salt, for example the hydrochloride.

The pharmacologically acceptable salts of the O-methylated hydroxyaporphines can be obtained in the usual manner, for example by neutralisation of the free bases with pharmacologically acceptable inorganic and organic acids, for example, hydrochloric acid, sulphuric acid, phosphoric acid, hydrobromic acid, acetic acid, tartaric acid, lactic acid, citric acid, malic acid, salicylic acid, malonic acid, maleic acid or succinic acid.

The following Examples are given for the purpose of illustrating the present invention:

EXAMPLE 1.

1,2,9,10-Tetramethoxyaporphine.

Variant A:

O-Methylation of (+)-2,9-dihydroxy-1,10-dimethoxyaporphine.

327 mg. (+)-2,9-Dihydroxy-1,10-dimethoxyaporphine are dissolved in a mixture of 2 ml. dimethyl formamide and 20 ml. toluene. The yellowish solution thus obtained is heated to 90°–95° C. and 3.5 ml. of a 1N solution of phenyl trimethyl ammonium hydroxide in methanol added thereto dropwise in the course of about 10 to 15 minutes, with vigorous stirring and the simultaneous distilling off of the methanol/toluene azeotrope. When the addition is finished, the reaction mixture is heated until the temperature of the distillate passing over has reached about 111° C. Heating is then continued under reflux for a further 15 to 30 minutes. According to the thin layer chromatogram, at the end of this reaction time practically no starting material is present. The reaction mixture is allowed to cool, precipitated phenyl trimethyl ammonium hydroxide is filtered off and the filtrate is evaporated under water pump vacuum. The dimethylaniline formed by the reaction is removed as far as possible at 70° C./0.1 mm. Hg on a rotary evaporator.

The residue is taken up in toluene and washed twice with a dilute aqueous solution of potassium hydroxide and subsequently with water. After drying the organic phase and stripping off the solvent, there is obtained a residue of a yellowish oil which is taken up in a little ethanol and mixed with somewhat more than the calculated amount of hydrogen bromide in the form of a 48% aqueous solution. Upon standing at ambient temperature the hydrobromide of (+)-1,2,9,10-tetramethoxyaporphine crystallises out; m.p. 221°–224° C. The yield is 366 mg. (84% of theory); $[\alpha]_D^{24} = +86.9°(0.2\%$ in ethanol).

Analysis: $C_{21}H_{26}BrNO_4$:
calculated: C 57.81%; H 6.01%; N 3.21%;
found: 57.61%; 5.88%; 3.31%

The combined aqueous phases are rendered just acidic with hydrochloric acid and subsequently mixed with ammonia. After extraction with chloroform, drying and removing the organic phase, there are obtained 43 mg. of a mixture of the two isomeric monomethylation products, i.e. 2-hydroxy-1,9,10-trimethoxyaporphine and 9-hydroxy-1,2,10-trimethoxyaporphine, which can be returned again to the methylation process.

When using dimethyl sulphoxide or hexamethyl phosphoric triamide instead of dimethyl formamide, under otherwise the same conditions, there are obtained yields of 70 and 85% of theory, respectively.

Variant B:

O-Methylation of (+)-2-hydroxy-1,9,10-trimethoxyaporphine.

6.5 g. (+)-2-Hydroxy-1,9,10-trimethoxyaporphine are dissolved, with warming, in 300 ml. of a mixture of toluene/ethanol (8:2 v/v). At a bath temperature of 90° to 95° C., 40 ml. of a 1N solution of phenyl trimethyl ammonium hydroxide in methanol are added dropwise within the course of about 10 minutes, with vigorous stirring and simultaneous distilling off of the toluene/ethanol azeotrope. After completion of the addition, the bath temperature is increased until a boiling temperature of 111° C. has been reached. Reflux boiling is continued for an hour, whereafter the thin layer chromatogram shows that no more starting material is present.

Working up is carried out in the manner described in Variant A above to give 6.1 g. (70% of theory) (+)-1,2,9,10-tetramethoxyaporphine hydrobromide; m.p. 221°–223° C.

Variant C:

O-Methylation of (±)-1,9-dihydroxy-2,10-dimethoxyaporphine.

In a manner analogous to that described above in Variant A, 327 mg. (±)-1,9-dihydroxy-2,10-dimethoxyaporphine in toluene/dimethyl formamide is reacted with 4 ml. of a 1N methanolic solution of phenyl trimethyl ammonium hydroxide. Corresponding working up and crystallisation of the residue from diethyl ether gives pure (±)-1,2,9,10-tetramethoxyaporphine in a yield of more than 75% of theory; m.p. 138°–139° C.

EXAMPLE 2.

N-n-Propyl-1,2,9,10-tetramethoxy-N-noraporphine tartrate.

O-Methylation of (±)-1-hydroxy-N-n-propyl-2,9,10-trimethoxy-N-noraporphine.

In a manner analogous to that described in Example 1, Variant A, 2 g. (±)-1-hydroxy-N-n-propyl-2,9,10-trimethoxy-N-noraporphine are reacted in a mixture of 15 ml. dimethyl formamide and 200 ml. toluene with 16.5 ml. of a 1N methanolic solution of phenyl trimethyl ammonium hydroxide. After working up, there are obtained 2.1 g. of a yellow syrup which, according to the thin layer chromatogram, consists of almost uniform O-methylation product. By mixing with an ethanolic solution of tartaric acid, there is obtained racemic N-n-propyl-1,2,9,10-tetramethoxy-N-noraporphine tartrate; m.p. 188°–189° C.

Not only the starting material, i.e. (±)-1-hydroxy-N-n-propyl-2,9,10-trimethoxy-N-noraporphine, but also the permethylated aporphine derivative obtained therefrom according to the present invention are new and pharmacologically interesting compounds which are also within the scope of the present invention.

The (±)-1-hydroxy-N-n-propyl-2,9,10-trimethoxy-N-noraporphine used as starting material is prepared in the following manner 1-(3',4'-Dimethoxybenzyl)-6-methoxy-7-benzyloxy-3,4-dihydroisoquinoline (see Tetrahedron, 23, 2563/1967), obtained from 27 g. of the corresponding hydrochloride, is mixed with 100 ml. 1-iodopropane. The reaction mixture is slowly heated to 80° to 85° C., with stirring and the exclusion of light, a solution first being obtained from which the propiodide then precipitates out. After a reaction time of 3 hours, the product is filtered off with suction and washed with acetone.

27 g. of the 1-(3',4'-dimethoxybenzyl)-2-n-propyl-6-methoxy-7-benzyloxy-3,4-dihydroisoquinoline iodide thus obtained are suspended in 500 ml. methanol and mixed portionwise at about 10° C. with a total of 6 g. sodium borohydride, the compound thereby going into solution. Thereafter, the greater part of the solvent is distilled off in a vacuum and allowed to crystallise from methanol at 0° C. The crystals are filtered off with suction and then washed with isopropanol. There are obtained 17.4 g. (±)-1-(3',4'-dimethoxybenzyl)-2-n-propyl-6-methoxy-7-benzyloxy-1,2,3,4-tetrahydroisoquinoline; m.p. 71°–73° C.

15 g. of the tetrahydroisoquinoline thus obtained are dissolved in 75 ml. glacial acetic acid. After freezing the solution in an ice-bath, 30 ml. concentrated nitric acid are added thereto in 6 ml. portions at about 5° C. in the course of 5 minutes. Thereafter, the reaction mixture is poured on to ice, rendered alkaline with a concentrated aqueous solution of ammonia and extracted with chloroform. After drying and stripping off the chloroform phase and crystallising the residue from methanol, there are obtained 10.5 g. (±)-1-(3',4'-dimethoxy-6'-nitrobenzyl)-2-n-propyl-6-methoxy-7-benzyloxy-1,2,3,4-tetrahydroisoquinoline; m.p. 119°–120° C.

10 g. of the nitro compound thus obtained are dissolved in 300 ml. 80% aqueous ethanol and acidified with dilute hydrochloric acid. The pale brown solution obtained is hydrogenated at ambient temperature in the presence of 5 g. palladium-charcoal, the take up of hydrogen being finished after 30 minutes. The reaction mixture is filtered and the filtrate is evaporated in a vacuum. The residue is rendered alkaline with ammonia and then extracted with chloroform. After working up in the usual manner, there is obtained (±)-1-(3',4'-dimethoxy-6'-aminobenzyl)-2-n-propyl-6-methoxy-7-hydroxy-1,2,3,4-tetrahydroisoquinoline in the form of a syrup which is further reacted without purification. The crude product is taken up in 150 ml. 20% sulphuric acid and, while cooling with ice and stirring, a solution of 3.16 g. sodium nitrite in 15 ml. water is added thereto dropwise. The reaction mixture is further stirred for 30 minutes and then 25 g. copper powder added thereto portionwise at 0° C. The reaction mixture is further stirred for 1 hour at ambient temperature, filtered and the filtrate rendered alkaline with ammonia. It is extracted with chloroform. After drying and stripping off the organic phase, the residue is chromatographed on silica gel, using chloroform as elution agent. There are obtained 2.1 g. of thin layer chromatographically uniform (±)-1-hydroxy-6-n-propyl-2,9,10-trimethoxy-N-noraporphine in the form of a yellowish foam; NMR CDCl$_3$, δ in ppm: 8.01, 6.80, 6.54 (each 1 H,s), 3.95 (3×OCH$_3$). 2.2–3.2 (m), 1.6 (m, CH$_2$), 0.99 (m, CH$_3$).

EXAMPLE 3.

(−)-10,11-Dimethoxyaporphine.

O-Methylation of (−)-10,11-dihydroxyaporphine (apomorphine).

1.7 g. (−)-10,11-Dihydroxyaporphine are dissolved in 15 ml. dimethyl formamide. After the addition of 130 ml. toluene, the mixture is heated to 110° C. (bath temperature) and, within the course of 30 minutes, 25.6 ml. of a 1N methanolic solution of phenyl trimethyl ammonium hydroxide added thereto dropwise, with vigorous stirring and the simultaneous distilling off of the toluene/alcohol azeotrope. After completion of the addition, the bath temperature is gradually increased to 130° C. As soon as the temperature of the distillate passing over has reached 110°–111° C., a further 12.5 ml. of the above-described methylation solution are added thereto. The reaction mixture is subsequently heated under reflux for 1 hour and then worked up in a manner analogous to that described in Example 1, Variant A, to give (−)-10,11-dimethoxyaporphine in the form of a yellowish syrup which is purified chromatographically on basic aluminium oxide (activity stage III) using methylene chloride/petroleum ether (1:1 v/v) as elution agent, the yield being 1.555 g. (83% of theory); NMR spectrum (CDCl$_3$) δ 2.5 (3H, s, N—CH$_3$), 3.65 (3H,s, O—CH$_3$), 3.83 (3H, s, O—CH$_3$), 6.63–7.27 (4H, m), 8.1 (1H,dd, C—1—H) ppm.

What we claim is

1. Process for the O-methylation of hydroxyaporphines, wherein the phenolic hydroxyl groups of a compound of the general formula

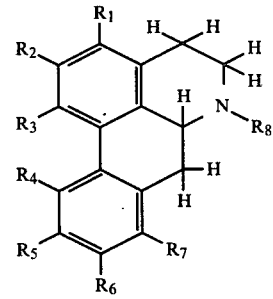

in which at least one of the symbols $R_1$ to $R_7$ signifies a hydroxyl group, whereas the other symbols represent hydrogen atoms or substituents which are inert under the reaction conditions and $R_8$ is a lower alkyl radical, are O-methylated in an inert solvent with a compound of the general formula

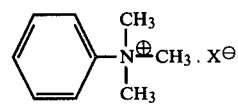

in which $X^-$ is a hydroxyl group or a lower alkoxy radical, whereafter the reaction product is isolated and, if desired, converted into a pharmacologically acceptable salt.

2. Process according to claim 1, wherein the alkylation agent used is phenyl trimethyl ammonium methylate or phenyl trimethyl ammonium ethylate.

3. Process according to claim 1 or 2, wherein the O-methylation is carried out at a temperature of from 100° to 150° C.

4. Process according to claim 3, wherein the O-methylation is carried out at a temperature of from 110° to 135° C.

5. Process according to claim 1, wherein the solvent used is a mixture of a hydrocarbon and a polar solvent.

6. Process according to claim 5, wherein the solvent used is a mixture of toluene and/or xylene with dimethyl formamide, dimethyl sulphoxide and/or hexamethyl phosphoric triamide.

7. Process according to claim 5 or 6, wherein the proportion of polar solvent in the solvent mixture is from about 10 to 20% by volume.

8. Process according to claim 1, wherein 1.25 to 2 moles of O-methylating agent are used for each phenolic hydroxyl group to be methylated.

* * * * *